(12) United States Patent
De Man et al.

(10) Patent No.: US 7,280,631 B2
(45) Date of Patent: Oct. 9, 2007

(54) STATIONARY COMPUTED TOMOGRAPHY SYSTEM AND METHOD

(75) Inventors: Bruno Kristiaan Bernard De Man, Clifton Park, NY (US); Samit Kumar Basu, Niskayuna, NY (US); Peter Michael Edic, Albany, NY (US); Robert Franklin Senzig, Germantown, WI (US); William Robert Ross, Scotia, NY (US); Xiaoye Wu, Rexford, NY (US); Colin Richard Wilson, Niskayuna, NY (US); Mark Ernest Vermilyea, Niskayuna, NY (US); Eugene Lino Saragnese, Delafield, WI (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 10/816,064

(22) Filed: Apr. 1, 2004

(65) Prior Publication Data

US 2005/0111610 A1 May 26, 2005

Related U.S. Application Data

(60) Provisional application No. 60/525,587, filed on Nov. 26, 2003.

(51) Int. Cl.
*G01N 23/00* (2006.01)
(52) U.S. Cl. .............................. 378/10; 378/9
(58) Field of Classification Search .............. 378/4–20, 378/124, 135, 137, 122
See application file for complete search history.

(56) References Cited

U.S. PATENT DOCUMENTS

| | | | |
|---|---|---|---|
| 4,223,225 A | | 9/1980 | Laffitte et al. |
| 4,239,972 A | | 12/1980 | Wagner |
| 5,305,363 A | * | 4/1994 | Burke et al. ................. 378/4 |
| 5,377,249 A | * | 12/1994 | Wiesent et al. .............. 378/4 |
| 5,438,605 A | * | 8/1995 | Burke et al. ............... 378/135 |
| 5,654,995 A | * | 8/1997 | Flohr ......................... 378/10 |
| 6,243,438 B1 | * | 6/2001 | Nahaliel et al. ............ 378/19 |
| 6,266,553 B1 | | 7/2001 | Fluhrer et al. |
| 6,385,292 B1 | | 5/2002 | Dunham et al. |
| 6,731,716 B2 | * | 5/2004 | Mihara et al. ............... 378/4 |
| 2002/0085674 A1 | | 7/2002 | Price et al. |
| 2002/0094064 A1 | * | 7/2002 | Zhou et al. ............... 378/122 |
| 2003/0118155 A1 | * | 6/2003 | Ueno et al. .............. 378/177 |
| 2004/0213378 A1 | * | 10/2004 | Zhou et al. .............. 378/122 |

FOREIGN PATENT DOCUMENTS

| EP | 1 266 621 | 12/2002 |
|---|---|---|
| EP | 1277439 A1 | 1/2003 |
| WO | WO02067779 A1 | 9/2002 |

* cited by examiner

*Primary Examiner*—Hoon Song
(74) *Attorney, Agent, or Firm*—Jean K. Testa; Curtis B. Brueske (57) ABSTRACT

Configurations for stationary imaging systems are provided. The configurations may include combinations of various types of distributed sources of X-ray radiation, which generally include addressable emitter elements which may be triggered for emission in desired sequences and combinations. The sources may be ring-like, partial ring-like, or line-like (typically along a Z-axis), and so forth. Combinations of these are envisaged. Corresponding detectors may also be full ring detectors or partial ring detectors associated with the sources to provide sufficient coverage of imaging volumes and to provide the desired mathematical completeness of the collected data.

39 Claims, 10 Drawing Sheets

FIG. 31

STATIONARY COMPUTED TOMOGRAPHY SYSTEM AND METHOD

CROSS REFERENCE TO RELATED APPLICATIONS

This application is related to Provisional Application U.S. Ser. No. 60/525,587, filed Nov. 26, 2003 in the U.S. Patent and Trademark Office, the contents of which are incorporated herein by reference, and the benefit of priority to which is claimed under 35 U.S.C. 119(e).

BACKGROUND OF THE INVENTION

The present invention relates generally to the field of computed tomography imaging systems. More particularly, the invention relates to geometries and configurations for the stationary computed tomography systems in which a detector and distributed source element are fixedly positioned in an imaging system scanner.

Many applications exist for computed tomography imaging systems. Developed over recent decades, such imaging systems provide a powerful tool for imaging internal features of subjects of interest, typically presented as slices and volumes. In general, the systems consist of a source that directs radiation through the subject of interest onto a detector. Although, the source may be any type of radiation that is able to penetrate the subject of interest, special attention is given to an X-ray source in the description herein. The X-ray source and detector, in traditional systems, are mounted on a rotational gantry and spun at a relatively high rotational rate, such on the order of two rotations per second, although faster and slower speeds are also used. Measurements of the incident X-ray intensity on the detectors, are acquired at many locations during rotation and may be stored for later analysis and processing. The systems then compute useful reconstructed images by processing the acquired intensity measurements allowing determination of the location of features within the subject. While variants on this basic design have been proposed and are presently in use, current technologies exploit rotation of the source and detector, with selection of acquisition windows and special processing of the data serving to enhance clarity of the reconstructed images.

While such arrangements have proven extraordinarily useful in identifying features of interest within a subject, they are limited by the need to rotate the source and detector elements. Sources of X-rays typically have included conventional X-ray tubes which are somewhat weighty, and must be powered and cooled during the rotation. Detectors, similarly, are becoming increasingly voluminous, spanning the field of view of the imaging system at higher resolutions, and multiple rows to obtain significant amounts of data during an exam. Circuitry associated with the detectors must also be rotated to perform the data acquisition and initial processing. Engineering proficiency is required to produce a carefully balanced system with power and data transmission interconnects, along with the mechanisms to remove heat generated during operation.

There is a need, at present, for improved system designs in computed tomography. In particular, there is a significant need for a design which can lighten rotational loads, or even eliminate the need for rotation of system components all together. There is a particular need for systems that can generate high-quality images while reducing the mechanical, electrical, thermal and other problems associated with rotation of a source and a detector.

BRIEF DESCRIPTION OF THE INVENTION

The present invention provides novel geometries and configurations for computed tomography (CT) systems designed to respond to such needs. The technique may be applied in a wide range of settings, including medical diagnostics contexts, part inspection, parcel and baggage handling applications, and so forth. The present techniques allow for distributed X-ray sources and detectors to be incorporated into a system without the need to rotate the sources or the detectors.

Various useful configurations for distributed sources and detectors are provided, some of which may be used in conjunction with one another to improve image data quality, improve completeness in acquired data for reconstruction purposes, provide coverage for excellent reconstructed images, and so forth. The technique may be employed with a range of emitters or sources operating in accordance with various techniques, which can be specifically and uniquely addressed for producing beams of radiation for imaging examinations. Similarly, the technique can be used with a wide range of detector configurations, many of the geometries being based on detector elements of a conventional construction. While certain elements of the system may be rotated, such as collimators or other elements, the present technique permits principle elements, that is, the source and detector, to remain essentially stationary during examination sequences.

DETAILED DESCRIPTION OF SPECIFIC EMBODIMENTS

Figure 1:
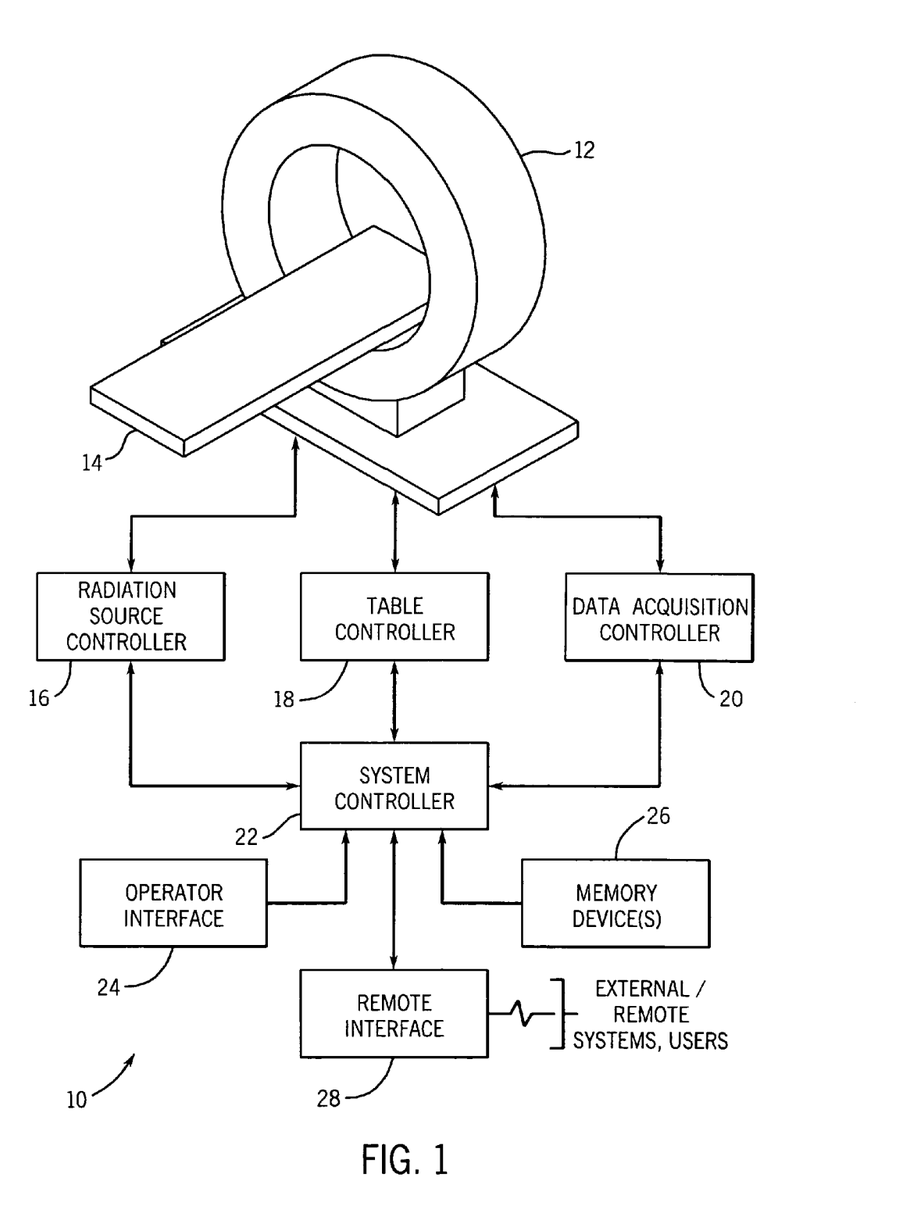
FIG. 1 is a diagrammatical representation of an exemplary stationary CT system in accordance with aspects of the present technique.

Turning now to the drawings, referring first to FIG. 1, a stationary computed tomography (CT) system is illustrated and designated generally by reference numeral 10. The CT system 10 comprises a scanner 12 formed of a support structure and internally containing one or more stationary and distributed sources of X-ray radiation (not shown in FIG. 1) and one or more stationary digital detectors (not shown in FIG. 1), as described in greater detail below. The scanner is configured to receive a table 14 or other support for a patient, or, more generally, a subject to be scanned. The table can be moved through an aperture in the scanner to appropriately position the subject in an imaging volume or plane scanned during imaging sequences.

The system further includes a radiation source controller 16, a table controller 18 and a data acquisition controller 20, which may all function under the direction of a system controller 22. The radiation source controller 16 regulates timing for discharges of X-ray radiation which is directed from points around the scanner 12 toward a detector segment on an opposite side thereof, as discussed below. In the present stationary CT arrangements, the radiation source controller 16 may trigger one or more emitters in a distributed X-ray source at each instant in time for creating multiple acquisitions of transmitted X-ray intensity data. In certain arrangements, for example, the X-ray radiation source controller 16 may trigger emission of radiation in sequences so as to collect adjacent or non-adjacent acquisitions of transmitted X-ray intensity around the scanner. Many such measurements may be collected in an examination sequence, and data acquisition controller 20, coupled to detector elements as described below receives signals from the detector elements and processes the signals for storage and later image reconstruction. Table controller 18, then, serves to appropriately position the table and subject in a plane in which the radiation is emitted, or, in the present context, generally within a volume to be imaged. The table may be displaced between imaging sequences or during certain imaging sequences, depending upon the imaging protocol employed.

System controller 22 generally regulates the operation of the radiation source controller 16, the table controller 18 and the data acquisition controller 20. The system controller 22 may thus cause radiation source controller 16 to trigger emission of X-ray radiation, as well as to coordinate such emissions during imaging sequences defined by the system controller. The system controller may also regulate movement of the table in coordination with such emission so as to collect transmitted X-ray intensity measurement data of volumes of particular interest, or in various modes of imaging, such as helical modes. The system controller 22 also receives data acquired by data acquisition controller 20 and coordinates storage and processing of the data.

It should be borne in mind that the controllers, and indeed various circuitry described herein, may be defined by hardware circuitry, firmware or software. The particular protocols for imaging sequences, for example, will generally be defined by code executed by the system controllers. Moreover, initial processing, conditioning, filtering, and other operations required on the transmitted X-ray intensity data acquired by the scanner may be performed in one or more of the components depicted in FIG. 1. For example, as described below, detector elements will produce analog signals representative of depletion of a charge in photodiodes positioned at locations corresponding to pixels of the acquisition detector. Such analog signals are converted to digital signals by electronics within the scanner, and are transmitted to data acquisition controller 20. Partial processing may occur at this point, and the signals are ultimately transmitted to the system controller for further filtering and processing.

System controller 22 is also coupled to an operator interface 24 and to one or more memory devices 26. The operator interface may be integral with the system controller, and will generally include an operator workstation for initiating imaging sequences, controlling such sequences, and manipulating data acquired during imaging sequences. The memory devices 26 may be local to the imaging system, or may be partially or completely remote from the system. Thus, imaging devices 26 may include local, magnetic or optical memory, or local or remote repositories for imaged data for reconstruction. Moreover, the memory devices may be configured to receive raw, partially processed or fully processed data for reconstruction.

System controller 22 or operator interface 24, or any remote systems and workstations, may include software for image processing and reconstruction. As will be appreciated by those skilled in the art, such processing of CT data may be performed by a number of mathematical algorithms and techniques. For example, conventional filtered back-projection techniques may be used to process and reconstruct data acquired by the imaging system. Other techniques, and techniques used in conjunction with filtered back-projection may also be employed. A remote interface 28 may be included in the system for transmitting data from the imaging system to such remote processing stations or memory devices.

Figure 2:
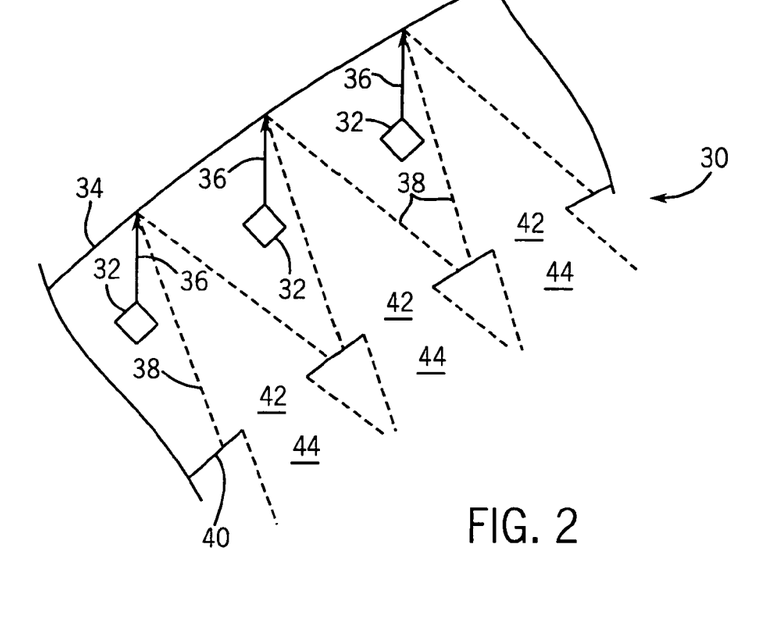
FIG. 2 is a diagrammatical representation of an exemplary distributed source for use with a system of the type illustrated in FIG. 1.

The scanner 12 of stationary CT system 10 preferably includes one or more distributed X-ray sources as well as one or more digital detectors for receiving radiation and processing corresponding signals to produce data. FIG. 2 illustrates a portion of an exemplary distributed X-ray source of the type that may be employed in the stationary CT system. As shown in FIG. 2, in an exemplary implementation, the distributed X-ray source 30 may include a series of electron beam emitters 32 that are coupled to radiation source controller 16 shown in FIG. 1, and are triggered by the source controller during operation of the scanner. The electron beam emitters 32 are positioned adjacent to a target 34. Upon triggering by the source controller, the electron beam emitters 32 may emit electron beams 36 toward target 34. The target 34, which may, for example, be a tungsten rail or element, emits X-ray radiation, as indicated at reference numeral 38, upon impact of the electron beams. The X-ray source may be operated in either reflection or transmission mode. In reflection mode as shown in FIG. 2, X-rays are meant to be produced primarily on the same side of the target as where the electrons impact. In transmission mode, X-rays are produced at the opposite side of the target. The X-ray beams 38 are directed, then, toward a collimator 40, which is generally opaque to the X-ray radiation, but which includes apertures 42. The apertures 42 may be fixed in dimension, or may be adjustable. Apertures 42 permit a portion of the X-ray beams to penetrate through the collimator to form collimated beams 44 that will be directed to the imaging volume of the scanner, through the subject of interest, and that will impact detector elements on an opposite side of the scanner.

A number of alternative configurations for emitters or distributed sources may, of course, be envisaged. Moreover, the individual X-ray sources in the distributed source may emit various types and shapes of X-ray beams. These may include, for example, fan-shaped beams, cone-shaped beams, and beams of various cross-sectional geometries. Similarly, the various components comprising the distributed X-ray source may also vary. In one embodiment, for example, a cold cathode emitter is envisaged which will be housed in a vacuum housing. A stationary anode is then placed in the housing and spaced apart from the emitter. This type of arrangement generally corresponds to the diagrammatical illustration of FIG. 2. Other materials, configurations, and principals of operations may, of course, be employed for the distributed source. The emission devices may be one of many available electron emission devices, for example, thermionic emitters, carbon-based emitters, photo emitters, ferroelectric emitters, laser diodes, monolithic semiconductors, etc.

As discussed in greater detail below, the present stationary CT techniques are based upon use of a plurality of distributed and addressable sources of X-ray radiation. Moreover, the distributed sources of radiation may be associated in single unitary enclosures or tubes or in a plurality of tubes designed to operate in cooperation. Certain of the source configurations described below are arcuate or ring-like in shape so as to positionable about the aperture in the scanner. Other sources are linear in configuration, so as to extend along the imaging volume, in the "Z direction" in terms of the conventional CT nomenclature. The individual sources are addressable independently and individually so that radiation can be triggered from each of the sources at points in time during the imaging sequence as defined by the imaging protocol. In other configurations, the sources are addressable in logical groups, for example pairs or triplets of emitters may be wired together. Where desired, more than one such source may be triggered concurrently at any instant in time, or the sources may be triggered in specific sequences to mimic rotation of a gantry, or in any desired sequence around the imaging volume or plane.

Figure 3:
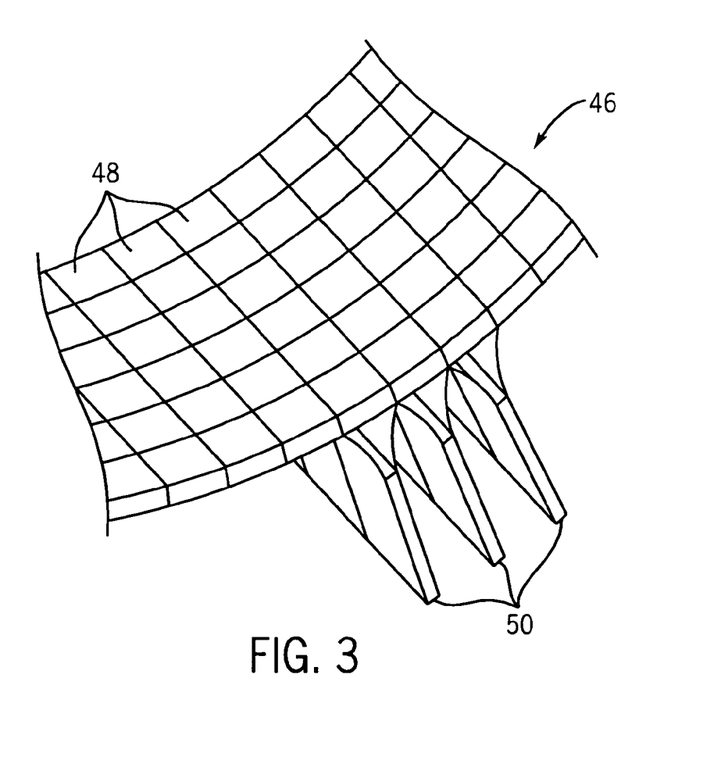
FIG. 3 is a diagrammatical representation of a portion of a detector for use with the system in FIG. 1.

A plurality of detector elements form one or more detectors which receive the radiation emitted by the distributed sources. FIG. 3 illustrates a portion of a detector which may be employed for the present purposes. Each detector may be comprised of detector elements with varying resolution to satisfy a particular imaging application. The detector arrangement may be generally similar to detectors used in conventional rotational CT systems, but is extended around a greater portion or the entire inner surface of the scanner. Particular configurations for the detector or detectors are summarized below. In general, however, the detector 46 includes a series of detector elements 48 and associated signal processing circuitry 50. Each detector element may include an array of photodiodes and associated thin film transistors. X-ray radiation impacting the detectors is converted to lower energy photons by a scintillator and these photons impact the photodiodes. A charge maintained across the photodiodes is thus depleted, and the transistors may be controlled to recharge the photodiodes and thus measure the depletion of the charge. By sequentially measuring the charge depletion in the various photodiodes, each of which corresponds to a pixel in the collected data for each acquisition, data is collected that encodes transmitted radiation at each of the pixel locations. This data is processed by the signal processing circuitry 50, which will generally convert the analog depletion signals to digital values, perform any necessary filtering, and transmit the acquired data to processing circuitry of the imaging system as described above. Although the detector has been described in terms of a scintillator-based energy-integrating device, direct conversion, photon counting, or energy discriminating detectors are equally suitable.

A large number of detector elements 48 may be associated in the detector so as to define many rows and columns of pixels. As described below, the detector configurations of the present technique position detector elements across from independently addressable distributed X-ray sources so as to permit a large number of view acquisitions to be collected for image reconstruction.

As will be appreciated by those skilled in the art, reconstruction techniques in CT systems vary in their use of acquired data, and in their techniques and assumptions for image reconstruction. It has been found, in the present technique, that a number of geometries are available for high-speed and efficient operation of a stationary CT system, which provide data for accurate image reconstruction. FIGS. 4-31 illustrate exemplary geometries and configurations for distributed sources and for detectors which are stationary in the CT scanner, but that can be used with conventional or improved image processing and image reconstruction algorithms.

Many of the presently contemplated geometries include 360-degree sources and/or detectors. However, certain of these concepts can be reduced to less expensive and equally or generally satisfactorily performing configurations by eliminating a portion of the complete ring in these structures. Depending upon the image reconstruction technique employed, for example, detectors extending around 180 degrees plus the fan angle of the emitted X-ray beams may be sufficient for excellent data collection and image construction. Moreover, for mechanical reasons, there may be a gap between sources and detectors at interfaces. Such gaps may be accounted for by addition measurements from sources and/or detectors, which account for the missing data. Moreover, the configurations described below are contemplated for both axial and helical scan modes. Depending upon the particular application, however, certain of the configurations may be more suited to one or the other of these modes, such as to the axial mode for medical applications and helical modes for applications such as baggage scanning. Finally, the sources and detectors described in the configurations below may have different diameters, sizes, extents, and so forth. Moreover, the sources and detectors may be comprised of linear or planar sections respectively, which approximate the configurations discussed below.

Figure 4:
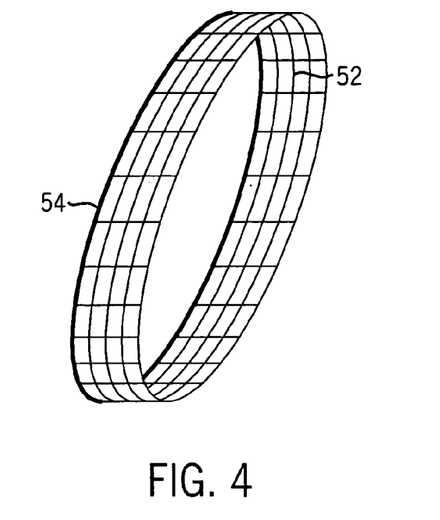
FIG. 4 is a diagrammatical representation of a first embodiment of a stationary CT configuration including a ring source and ring detector.

In a first configuration illustrated in FIG. 4, a ring detector 52 comprises a plurality of detector elements such as illustrated in FIG. 3, extending generally entirely around an imaging volume. A distributed source in the form of a ring source 54 is positioned adjacent to the ring detector 52 and includes a large number of individually addressable sources or emitters as described above. The sources can be triggered by the system controller to emit radiation toward the detector, generally at a diametrically opposed location, which radiation passes through the subject of interest, is attenuated by features of the subject of interest, and impacts the detector for data collection.

Figure 5:
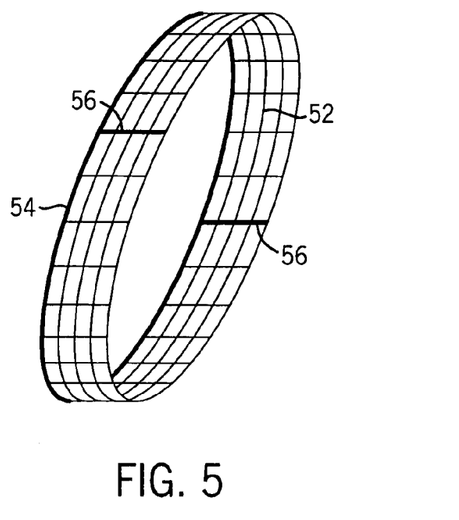
FIG. 5 is a further configuration employing a ring source, ring detector, and line sources.

The configuration of FIG. 5 includes a ring detector 52 of the type illustrated in FIG. 4, along with a ring source 54. The arrangement also includes a pair of line sources along the Z-direction as indicated by line sources 56. The single ring source is positioned on one side of the detector and the line sources 56 extend from the ring source to contribute to the completeness of the data collected by the system. The ring detector 52 may include gaps accommodating the line sources 56. While such line sources may increase the complexity of operation in data collection, they are believed potentially to improve the mathematical completeness of the collective data acquisitions. While two such line sources are illustrated in FIG. 5, this configuration may include as few as a single line source, or more than two line sources.

Figures 6, 7:
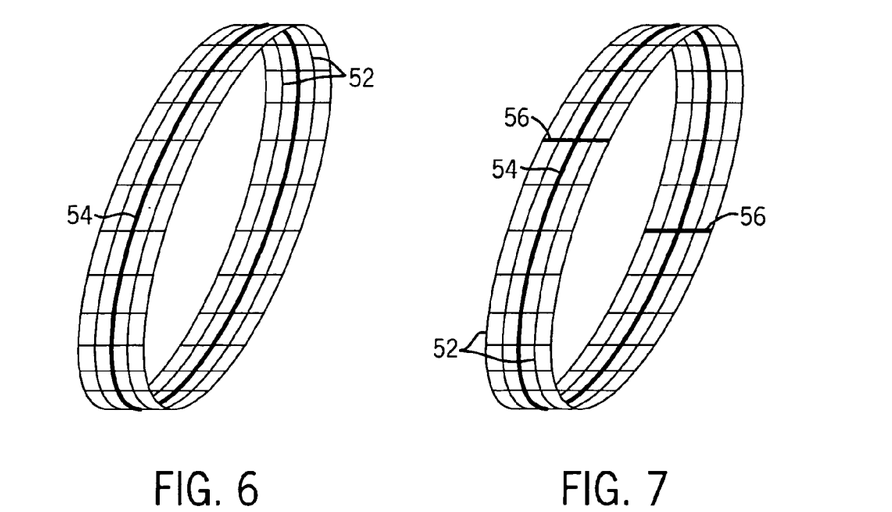
FIG. 6 is an alternative configuration employing a ring source between two ring detectors.
FIG. 7 is a diagrammatical representation of an alternative configuration employing a ring source between two ring detectors with line sources.

The configuration of FIG. 6 incorporates a pair of ring detectors 52 with a ring source 54 positioned therebetween. This configuration is believed to be particularly attractive for low-dose efficiency, and may be particularly useful in detecting certain substances of interest, such as explosives.

The configuration of FIG. 7 includes a pair of ring detectors 52, a ring source 54 and one or more line sources 56. The ring source is positioned between the ring detectors, and the line sources extend generally parallel to the ring detector. Gaps may be provided in the ring detectors to accommodate the line sources. The line sources are added to the configuration to measure additional data for mathematical completeness of the acquired data as in the case of the arrangement of FIG. 5.

Figure 8:
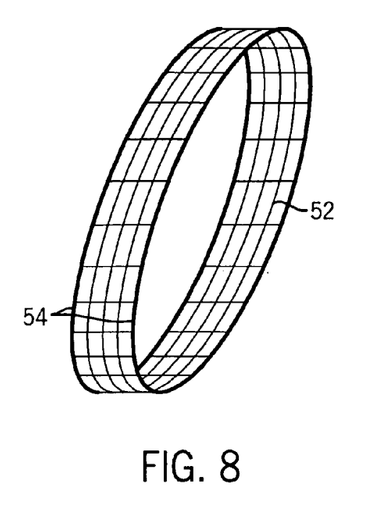
FIG. 8 is a diagrammatical representation of an alternative configuration employing a pair of ring sources with a ring detector.

FIG. 8 illustrates a further alternative embodiment in which two ring sources 54 are positioned in a flanking arrangement on either side of a ring detector 52. It is believed that this arrangement can provide reasonable data completeness, and that any missing regions of interest around the mid-plane of the scanner can be reduced. Moreover, the detector can be made smaller than in the case of the foregoing arrangement for the same axial coverage at the center of the field of view of the imaging system. Similarly, scatter can be significantly reduced due to the use of a smaller cone angle for the sources. A higher data acquisition sampling rate may be required with this arrangement if the same number of views is to be maintained for each source ring.

Figure 9:
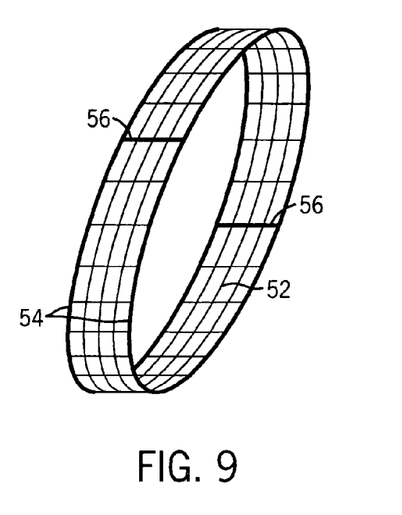
FIG. 9 is a diagrammatical representation of an alternative configuration employing a pair of ring sources and line sources with a ring detector.

The configuration of FIG. 9 includes a ring detector 52 flanked by a pair of ring sources 54 and including one or more line sources 56. As before, the line sources provide a means to acquire additional data, which add to the mathematical completeness of the collective data acquisition, and the source rings provide the advantages of the configuration of FIG. 8.

Figure 10:
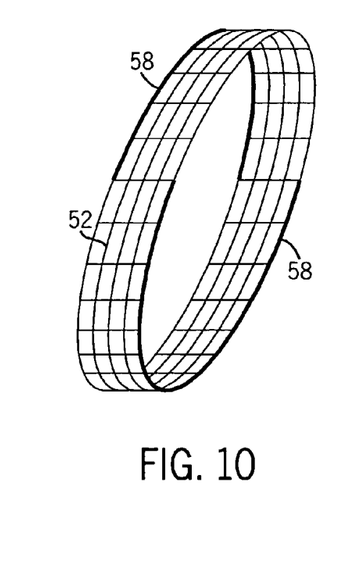
FIG. 10 is a diagrammatical representation of an alternative configuration employing a pair of partial ring sources with a ring detector.

The configuration of FIG. 10 is based upon a combination of partial ring sources 58 which flank a ring detector 52 of the type described above. The partial ring sources are illustrated as being two in number, although other numbers of partial ring sources may be included, and these may be positioned on alternating sides of the ring detector. It is believed that the configuration of FIG. 10 reduces the cost of the sources as compared to full ring sources, although somewhat less mathematically complete data may result. To provide partial ring sources on alternating sides of the ring detector, even numbers of partial ring sources would be employed, with better results being expected from two partial ring sources, and lesser results be expected from four partial ring sources.

Figure 11:
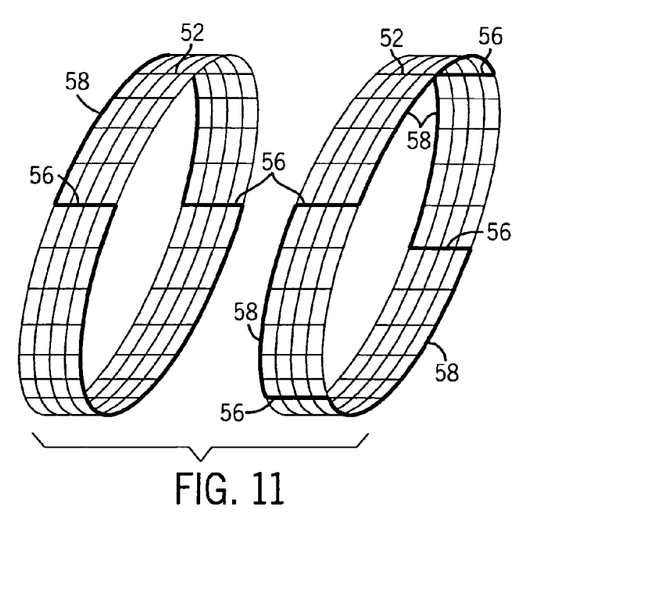
FIG. 11 is a diagrammatical representation of an alternative configurations employing partial ring sources and line sources with a ring detector.

The configuration of FIG. 11 is similar to that of FIG. 10, although the arrangement further includes line sources 56 in combination with the partial ring sources 58. As in the previous cases of the use of line sources 56, gaps may be provided in the ring detector 52 to permit radiation to be emitted from the line sources along the Z-axis. The line sources along the Z-axis add to the mathematical completeness of the collective data acquisition. In the illustration of FIG. 11, two or four such partial source rings may be employed, although this number may vary to greater numbers.

Figures 12, 14:
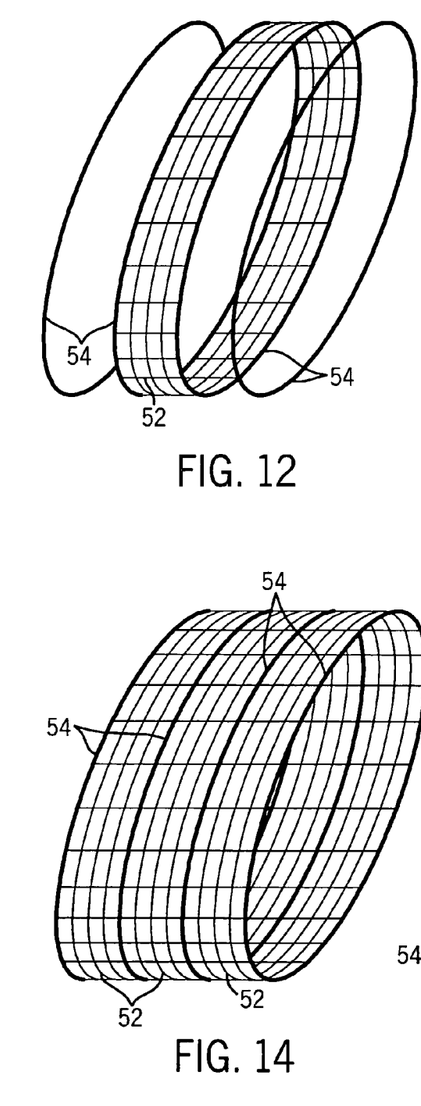
FIG. 12 is a diagrammatical representation of an alternative configuration employing a series of ring sources and a ring detector.
FIG. 14 is a diagrammatical representation of an alternative configuration employing a series of ring sources with a series of ring detectors.

The configuration of FIG. 12 employs a ring detector as in the previous arrangement, flanked by pairs of ring sources 54. In this embodiment, two such ring sources are provided immediately adjacent to the ring detector 52, and additional ring sources are provided at spaced-apart locations on either side thereof. It is anticipated that the outer rings may provide redundant data when used in conjunction with the inner rings. Similarly, the configuration of FIG. 13 employs ring sources and a ring detector in conjunction with a pair of line sources 56 in the Z-direction. As before, it is anticipated that the line sources 56 may aid in providing more complete data for image reconstruction.

Figures 13, 15:
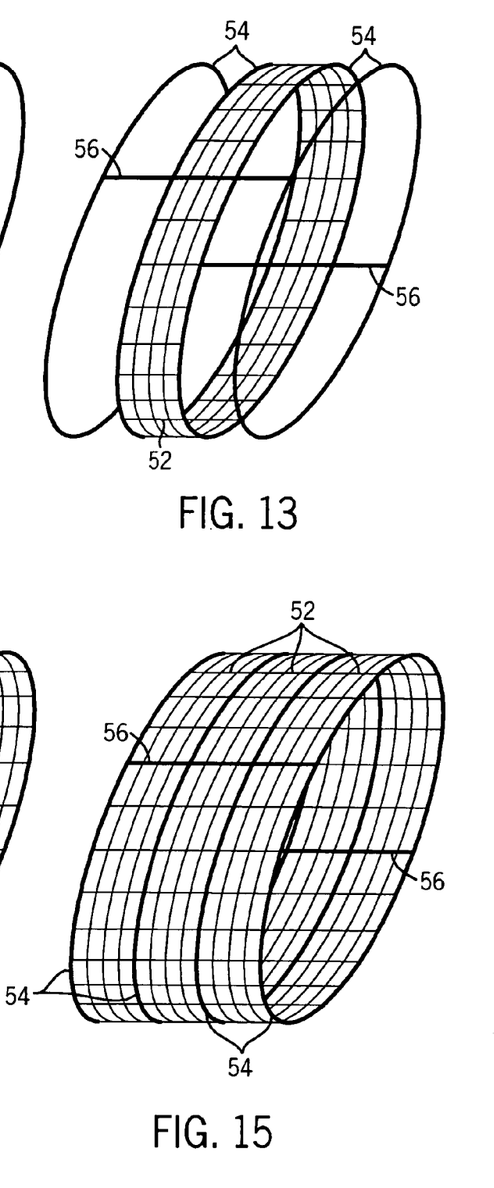
FIG. 13 is a diagrammatical representation of an alternative configuration employing a series of ring sources and line sources with a ring detector.
FIG. 15 is a diagrammatical representation of an alternative configuration employing a series of ring sources and line sources with a series of ring detectors.

The configuration of FIGS. 14 and 15 are analogous to those of FIGS. 12 and 13, although multiple ring detectors are illustrated as being positioned between the spaced-apart ring sources. As will be appreciated by those skilled in the art, the configuration of FIG. 14 and FIG. 15 result in lower required cone angles for the emitted radiation for given coverages of the subject in the Z-direction when compared to the configurations in FIG. 8 and FIG. 9. Where desired, the detectors 52 of the arrangement of FIG. 14 and FIG. 15 may have different resolutions, with a central detector having a higher resolution than the outer detectors. The arrangement of FIG. 15 is similar to that of FIG. 14, but adds line detectors along the axis for enhancing mathematical completeness of the acquired data.

Depending on the application, one or more of the ring sources 54 and one or more of the ring detectors 52 in FIG. 14 may be utilized for a certain imaging protocol. Several data acquisition schemes are envisioned where the resolution of the detectors may be configured depending on the number of ring detectors 52 and ring sources 54 utilized—minimizing the required electronics in the data acquisition system for the detector. The configurations utilizing the arrangement of FIG. 14 are applicable to the arrangement of FIG. 15; however, additional data is acquired using the available line sources 56.

Figure 16:
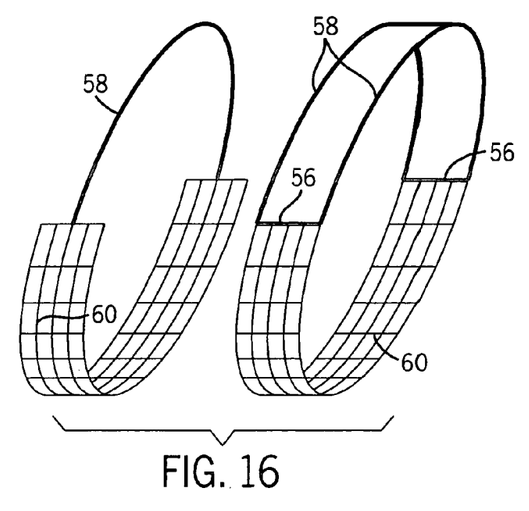
FIG. 16 is a diagrammatical representation of alternative configurations employing one or more partial ring sources, with line sources, and a partial ring detector.

The configurations of FIG. 16 include at least one partial ring source 58 in conjunction with a partial ring detector 60. The arrangements may also include one or more line sources 56 along the Z-axis. Arrangements such as those shown in FIG. 16 provide for coverage of relevant portions of the imaging volume, such as 180 degrees of the volume by the detector, and 180 degrees of the volume by the source. Advantages of such arrangements include the fact that the source and detector can be placed in the same general imaging plane. Data may be somewhat incomplete with certain of the arrangements, however.

Figure 17:
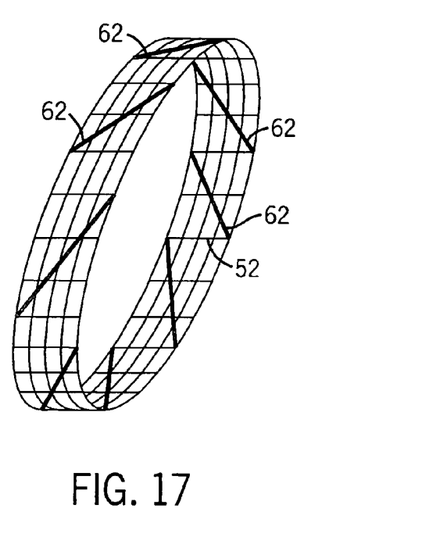
FIG. 17 is a diagrammatical representation of an alternative configuration employing a series of line/arc sources and a ring detector.

The configuration of FIG. 17 includes a generally ring-like detector 52 and obliquely placed arcuate partial ring sources 62. The sources are adapted to emit radiation through the detector, which may be provided with slots or openings for accommodating the sources. The resulting structure provides a generally arcuate profile, a linear profile, a sinusoidal, a tilted circle, or two tilted circles. The design could be highly flexible from a mathematical completeness of the data acquisition standpoint.

Figure 18:
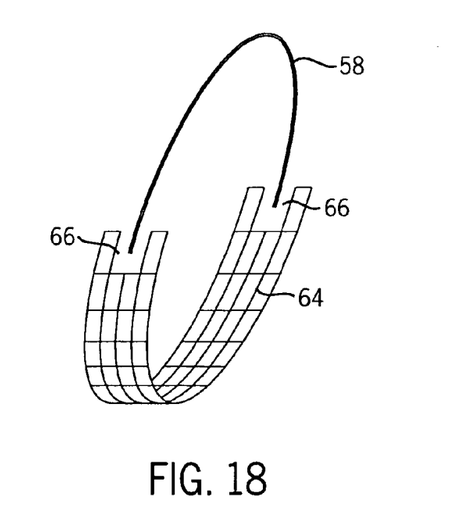
FIG. 18 is a diagrammatical representation of an alternative configuration employing a partial ring source and a partial ring detector in a notched configuration.

FIG. 18 illustrates an exemplary configuration comprising a modified partial ring detector as indicated by reference numeral 64. A partial ring source 58 is positioned to extend within notches 66 of the detector. The arrangement of FIG. 18 permits both the source and the detector to cover more than 180 degrees of the imaging volume. In a preferred configuration, the source would cover at least 180 degrees plus the fan angle of radiation emitted by the independently addressable and distributed sources.

Figure 19:
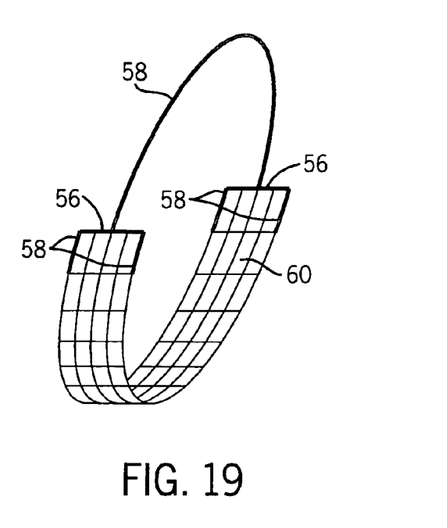
FIG. 19 is a diagrammatical representation of an alternative configuration employing a partial ring source and line/arc sources, some partially overlapping a partial ring detector.

The configuration of FIG. 19 is similar to that of FIG. 18, but enables the coverage of additional volume by the combination of multiple partial ring sources 58 with line sources along the Z axis, as indicated at reference numeral 56. The composite source, then, may cover more than 180 degrees of the imaging volume, and preferably 180 degrees plus a radiation fan angle, or more. The stationary detector is then a partial ring 60 as described above. This too may cover more than 180 degrees of the imaging volume.

Figure 20:
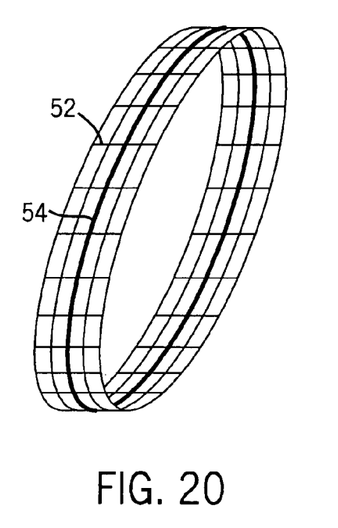
FIG. 20 is a diagrammatical representation of an alternative configuration employing a ring source and ring detector.

The configuration of FIG. 20 is somewhat similar to that of FIG. 6 above. The configuration consists of a ring detector 52 and a ring source 54. In the arrangement of FIG. 20, however, the detector is provided as a single unit without a central gap. The central detector elements would be physically configured to permit the distributed source 54 to emit radiation through the detector at one side, to be detected by detector elements on an opposite side of the arrangement.

Figure 21:
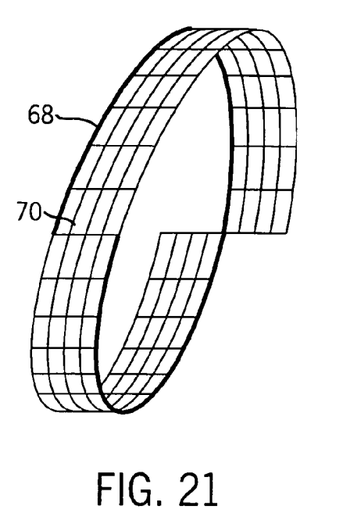
FIG. 21 is a diagrammatical representation of an alternative configuration employing a helical single-turn ring source and ring detector.

The configuration of FIG. 21 includes a helical source 68 placed adjacent to a helical detector 70. The source and detector may be generally of similar configuration to the configurations described above, but the helical arrangement illustrated in FIG. 21 permits for scanning in a manner that corresponds to conventional helical volumetric acquisition. Accordingly, the arrangement of FIG. 21 may be used to obtain data acquisition results similar to those obtainable via the configuration of FIG. 6 but with table translation. The configuration of FIG. 21 permits such acquisition without any missing portions or slabs of the imaging volume.

Figure 22:
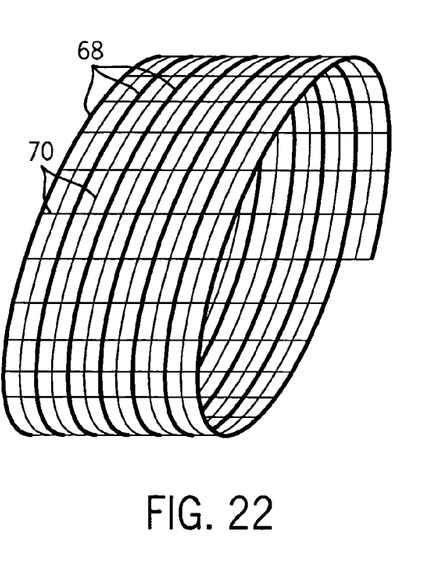
FIG. 22 is a diagrammatical representation of an alternative configuration employing a helical multiple-turn ring source and ring detector.

The configuration of FIG. 22 is similar to that of FIG. 21, but wherein the helical source 68 forms a plurality of turns around the imaging volume, as does the juxtaposed helical detector 70. The arrangement of FIG. 22 provides relatively complete data except at edges of the helix, and except at gaps between the source and detector.

Figure 23:
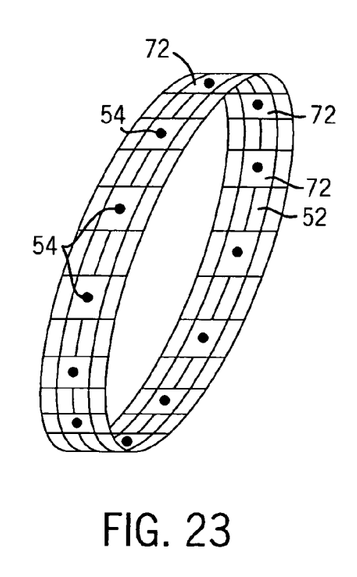
FIG. 23 is a diagrammatical representation of an alternative configuration employing a ring source configured to direct radiation through openings in a ring detector.

In another configuration illustrated in FIG. 23, a ring-like source 54 containing a plurality of independently addressable emitting sources represented by dots in the FIG. 23, is placed around a ring detector 52. The resulting arrangement is similar to that of FIG. 6. However, in the arrangement of FIG. 23, the detector is provided with apertures 72 through which the source can emit radiation. The arrangement permits for additional data to be collected between the locations where the distributed source emits through the detector.

Figure 24:
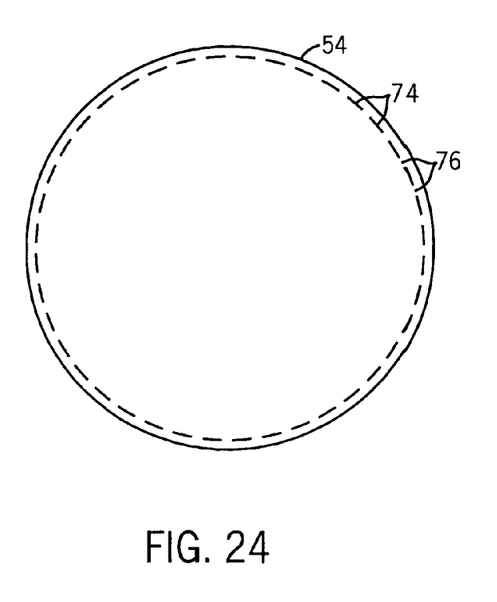
FIG. 24 is a diagrammatical representation of an alternative configuration employing a ring source configured to direct radiation through slits in a ring detector.

In a somewhat different configuration illustrated in FIG. 24, a ring source 54 at least partially surrounds a ring detector illustrated as including a plurality of segments 74. The segments are separated from one another by slits or openings 76. In practice, one or more such ring sources may be used. The source emits radiation through the slits 76, which may be generally oriented along the Z-axis.

Figure 25:
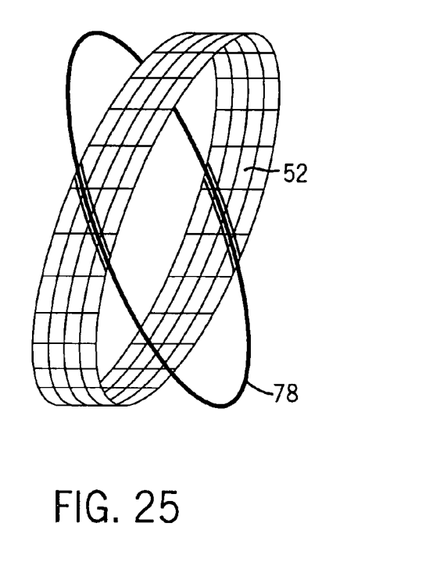
FIG. 25 is a diagrammatical representation of an alternative configuration employing a tilted ring source and ring detector.
Figures 26, 27:
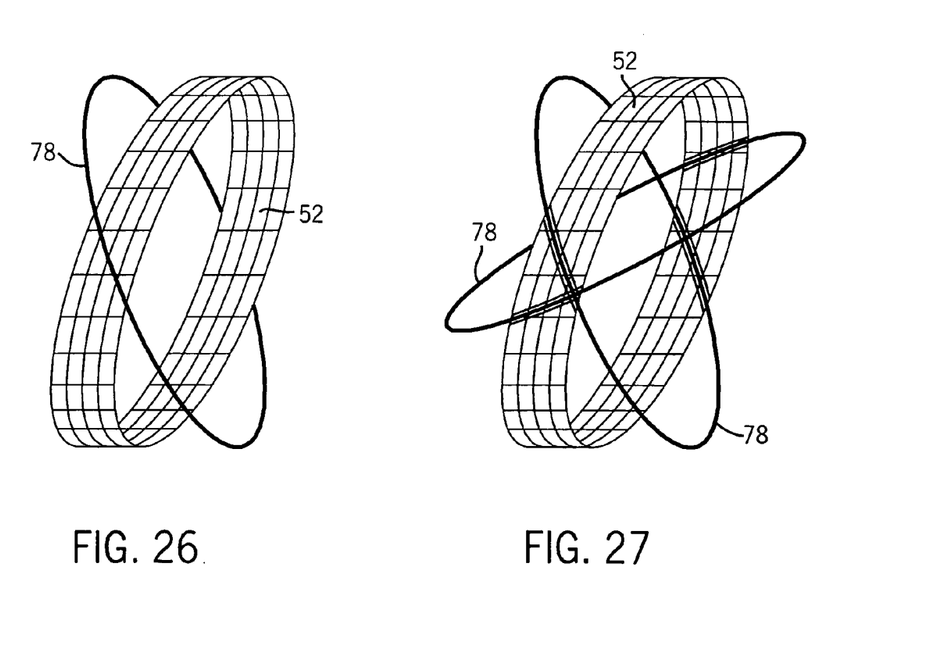
FIG. 26 is a diagrammatical representation of an alternative configuration employing a further configuration for a tilted ring source and ring detector.
FIG. 27 is a diagrammatical representation of an alternative configuration employing two tilted ring sources and a ring detector.
Figure 28:
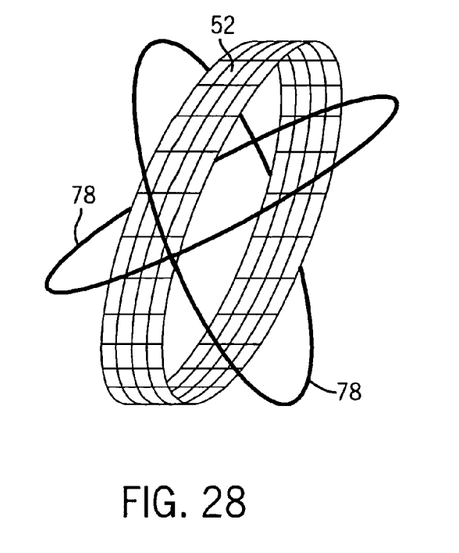
FIG. 28 is a diagrammatical representation of an alternative configuration again employing two tilted ring sources and a ring detector.

FIGS. 25-28 illustrate exemplary configurations that comprise tilted ring-like sources, as indicated by reference numeral 78 used in conjunction with a ring-like detector 52. In the arrangement of FIG. 25, for example, the detector is configured to provide space for emission of radiation at locations where the ring source crosses the detector in a manner similar to that discussed above with reference to FIG. 17. In the alternative arrangement of FIG. 26, the ring detector 52 is employed with a tilted ring source 78, but does not provide for passage for radiation emitted through the detector. In the alternative configuration of FIG. 27, two tilted ring sources 78 are employed in a manner similar to that illustrated in FIG. 25, with a ring detector 52. In this embodiment, passages provide permitted emission of radiation through the ring detector as mentioned above with respect to FIG. 25. In the configuration of FIG. 28, two ring sources 78 are again employed, but no passage is provided for emission of radiation through the ring detector 52 in a manner similar to that described above in FIG. 26. Although the sources in FIGS. 25-28 are shown as ring-like, they may be truncated and comprised of linear segments. Moreover, in FIG. 26 and FIG. 28, the source sections where the emitted radiation is blocked by the detector may be omitted.

Figure 29:
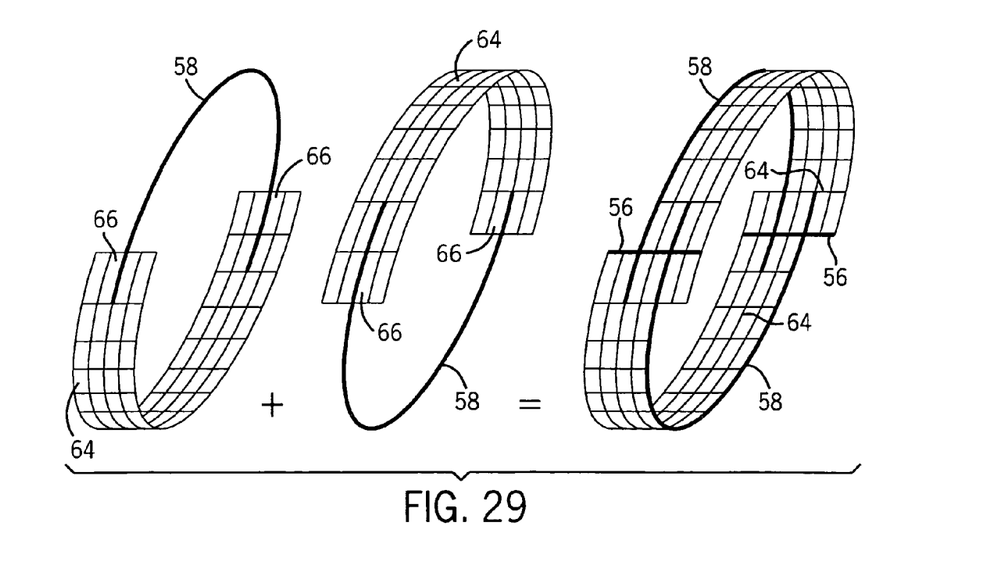
FIG. 29 is a diagrammatical representation of an alternative configuration employing a combination of partial ring sources and ring detectors in complimentary notched configurations.

The arrangement of FIG. 29 is effectively a combination of two notched detectors and corresponding source elements of the type illustrated above with regard to FIG. 18. That is, two notched detectors 64, presenting notches 66 for receiving a partial ring source 58 are combined end-to-end to provide generally complete arrangement around the imaging volume. The arrangement of FIG. 29 is believe to present advantages in terms of the mathematical completeness of the acquired data. Moreover, line sources 56 extending along the Z-axis may be added to the arrangement to improve data completeness as illustrated.

Figure 30:
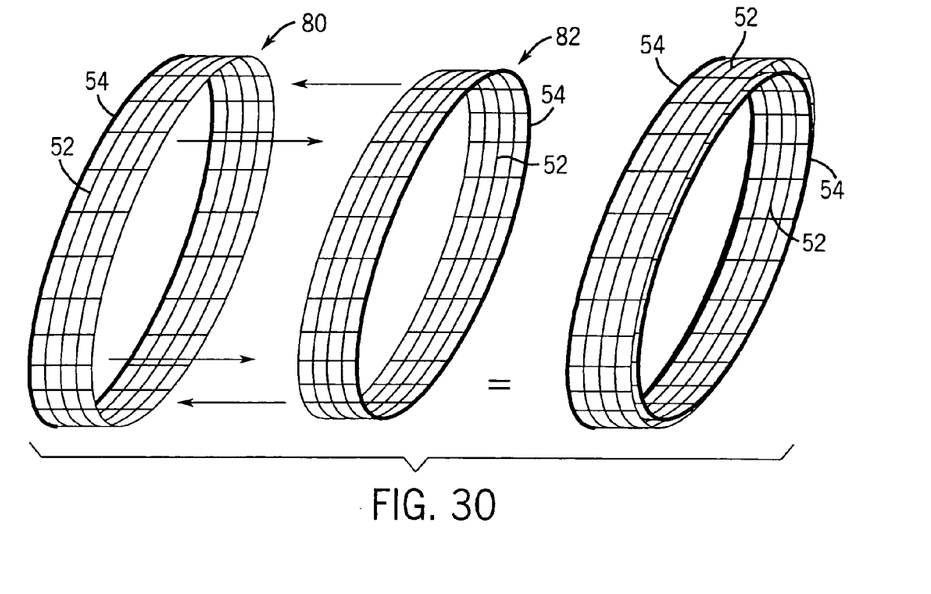
FIG. 30 is a diagrammatical representation of an alternative configuration employing a ring source and ring detector arrangement for telescoping or a combined interaction.

The arrangement of FIG. 30 includes a pair of ring sources 54 associated with respective ring detectors 52. The pairs of sources and detectors, designated by reference numerals 80 and 82 in FIG. 30 are of different diameters, permitting telescoping movement of one arrangement within the other. In some respects, the arrangement of FIG. 30 resembles the double ring source arrangement of FIG. 8, but wherein the detector is split into two concentric parts to allow adaptive Z-axis coverage. Such adaptive coverage may permit lower doses and may reduce scatter in examinations where only small Z axis coverage is desired. This arrangement is not limited to pairs of ring sources and ring detectors, but may include 2 or more ring sources and ring detectors.

Figure 31:
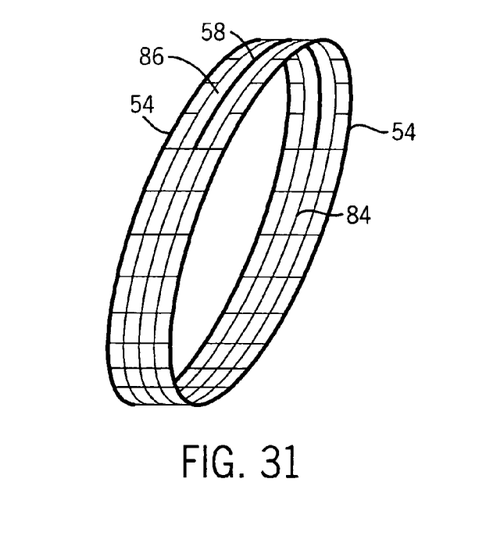
FIG. 31 is a diagrammatical representation of an alternative configuration employing a combination of ring and partial ring sources and a ring detector.

A further configuration, illustrated in FIG. 31, comprises multiple ring sources, two illustrated in the figure, as indicated by reference numeral 54, in combination with a partial ring source 58. A modified ring detector, designated by reference numeral 84, is provided between the ring sources 54. The modified detector 84 includes an opening 86 for accommodating the partial ring source 58. The arrangement of FIG. 31, and arrangements of this type including a combination of ring sources and partial ring sources may provide for more mathematical completeness in the acquired data than the arrangements in the foregoing configurations. To further improve the mathematical completeness of the measured data, line sources extending along the Z-axis can be included in this configuration; however, they are not shown in FIG. 31.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A volumetric stationary CT system comprising:
   at least one stationary detector extending generally around at least a portion of an imaging volume;
   at least one stationary distributed X-ray source placed proximal to the at least one stationary detector; and
   a source controller for triggering one or more emitters in the at least one stationary distributed X-ray source for acquiring volumetric data by the at least one stationary detector,
   wherein the at least one stationary detector and the at least one stationary distributed X-ray source are configured to cooperate to contribute towards mathematical completeness of acquired volumetric data for image reconstruction, and wherein the at least one stationary distributed X-ray source includes at least two full ring sources, wherein the at least one stationary detector includes a pair of ring detectors and wherein at least one ring source of the at least two full ring sources is positioned between the pair of ring detectors.

2. The system of claim 1 further comprising one or more line sources extending at least along a Z-direction to increase mathematical completeness in acquired volumetric data for image reconstruction.

3. The system of claim 1, wherein the at least one stationary detector includes one or more ring detectors placed between two or more ring sources.

4. The system of claim 3 further comprising one or more line sources extending at least along a Z-direction to increase mathematical completeness in acquired volumetric data for image reconstruction.

5. The system of claim 3, wherein the at least one stationary detector comprises one full ring detector placed between two full ring sources.

6. The system of claim 5 further comprising one or more line sources extending at least along a Z-direction to increase mathematical completeness in acquired volumetric data for image reconstruction.

7. The system of claim 3, wherein the at least two ring sources are placed immediately adjacent to the stationary detector and additional ring sources are placed at spaced-apart locations on elmer aide thereof.

8. The system of claim 7 further comprising one or more line sources extending at least along a Z-direction to increase mathematical completeness in acquired volumetric data for image reconstruction.

9. The system of claim 3, wherein the two or more ring sources include a plurality of spaced-apart ring sources for emitting radiation, and the at least one stationary detector includes a plurality of ring detectors being positioned between the spaced-apart ring sources for receiving the radiation.

10. The system of claim 9 further comprising two or more line sources extending at least along a Z-direction to increase mathematical completeness in acquired volumetric data for image reconstruction.

11. The system of claim 1 further comprising one or more partial ring sources and wherein the at least one stationary detector includes one or more ring detectors positioned between two or more ring sources and includes the one or more partial ring sources.

12. The system of claim 1, wherein the at least one stationary detector includes one or more ring detectors positioned between two or more ring sources, wherein the one or more ring detectors and the two or more ring sources comprise different diameters for permitting a telescoping movement of the one or more ring detectors with the two or more ring sources.

13. The system of claim 1 further comprising detector elements having varying resolutions and towing the at least one stationary detector, wherein the at least one stationary detector extends generally around a portion of an inner surface of the volumetric stationary CT system.

14. A volumetric stationary CT system comprising:
   at least one stationary detector extending generally around at least a portion of an imaging volume;
   at least one stationary distributed X-ray source placed proximal to the at least one stationary detector;
   one or more line sources extending at least along a Z-direction; and
   a source controller for triggering one or more emitters in the at least one stationary distributed X-ray source for acquiring volumetric data by the at least one stationary detector,
   wherein the at least one stationary detector, the at least one stationary distributed X-ray source, and the one or more line sources are configured to cooperate to contribute towards mathematical completeness of acquired volumetric data for image reconstruction.

15. A volumetric stationary CT system comprising:
   at least one stationary ring detector extending generally around at least a portion of an imaging volume;
   more than one partial ring sources flanking the at least one stationary ring detector on alternating sides of the at least one stationary ring detector and configured to emit radiation toward the ring detector; and
a source controller for triggering one or more emitters in the more than one partial ring sources for acquiring volumetric data by the at least one stationary ring detector,
wherein the at least one stationary ring detector, and the more than one partial ring sources are configured to cooperate to contribute towards mathematical completeness of acquired volumetric data for image reconstruction.

16. The system of claim 15 further comprising one or more line sources extending at least along a Z-direction to increase mathematical completeness in acquired volumetric data for image reconstruction.

17. The system of claim 15, wherein the at least one stationary ring detector includes one or more notched detectors.

18. The system of claim 17, wherein the one or more notched detectors include a partial ring detector, and wherein the more than one partial ring sources extend within notches of the partial ring detector.

19. The system of claim 17 further comprising one or more line sources extending at least along a Z-direction to increase mathematical completeness in acquired volumetric data for image reconstruction.

20. The system of claim 17, wherein the one or more notched detectors include at least two notched detectors for receiving the more than one partial ring sources and configured to be combined along the Z-direction to generally surround the imaging volume.

21. The system of claim 20 further comprising one or more line sources extending at least along a Z-direction to increase mathematical completeness in acquired volumetric data for image reconstruction.

22. A volumetric stationary CT system comprising:
at least one stationary detector extending generally around at least a portion of an imaging volume;
at least one stationary distributed X-ray source placed proximal to the at least one stationary detector; and
a source controller for triggering one or more emitters in the at least one stationary distributed X-ray source for acquiring volumetric data by the at least one stationary detector,
wherein the at least one stationary detector and the at least one stationary distributed X-ray source are configured to cooperate to contribute towards mathematical completeness of acquired volumetric data for image reconstruction, wherein the at least one stationary detector includes a helical detector, and wherein the at least one stationary distributed X-ray source includes a helical source placed adjacent to the helical detector.

23. The system of claim 22, wherein at least one of the helical source and the helical detector forms a plurality of turns around the imaging volume.

24. An X-ray imaging system for scanning a volume to be imaged, the system comprising:
at least one stationary distributed X-ray source extending generally around at least a portion of an imaging volume and configured to emanate an X-ray radiation;
at least one stationary detector for receiving the X-ray radiation after attenuation in the imaging volume and placed proximal to the at least one stationary distributed X-ray source;
a control circuit operably coupled to the at least one distributed X-ray source, wherein the control circuit is configured for triggering one or more emitters in the at least one stationary distributed X-ray source for acquiring volumetric data by the at least one stationary detector;
a processing circuit operably coupled to the at least one detector and configured to receive the plurality of projection images and to form one or more reconstructed slices representative of the volume being imaged; and
an operator workstation operably coupled to the processing circuit configured to display the one or more reconstructed slices,
wherein the at least one stationary detector and the at least one stationary distributed X-ray source are configured to cooperate to contribute towards mathematical completeness of acquired volumetric data for image reconstruction,
wherein the at least one stationary distributed X-ray source includes at least two full ring sources, wherein the at least one stationary detector includes a pair of ring detectors and wherein at least one ring source of the two or more full ring sources is positioned between the pair of ring detectors.

25. The system of claim 24 further comprising one or more line sources extending at least along a Z-direction to increase mathematical completeness in acquired volumetric data for image reconstruction.

26. The system of claim 24, wherein the at least one stationary detector includes one or more ring detectors placed between two or more ring sources.

27. The system of claim 26, wherein the at least one stationary detector comprises one full ring detector placed between two full ring sources.

28. The system of claim 26, wherein the at least two ring sources are placed immediately adjacent to the stationary detector and additional ring sources at spaced-apart locations on either side thereof.

29. The system of claim 26, wherein the two or more ring sources include a plurality of spaced-apart ring sources for emitting radiation, and the at least one stationary detector includes a plurality of ring detectors being positioned between the spaced-apart ring sources for receiving the radiation.

30. The system of claim 24 further comprising one or more partial ring sources and wherein the at least one stationary detector includes one or more ring detectors positioned between two or more ring sources and includes one or more partial ring sources.

31. The system of claim 24, wherein the at least one stationary detector includes one or more ring detectors positioned between two or more ring sources, wherein the one or more ring detectors and the two or more ring sources comprise different diameters for permitting a telescoping movement of the one or more ring detectors with the two or more ring sources.

32. The system of claim 24 further comprising one or more line sources extending at least along a Z-direction to increase mathematical completeness in acquired volumetric data for image reconstruction.

33. The system of claim 24, wherein the at least one stationary detector includes a ring detector and wherein the at least one stationary distributed X-ray source includes one or more partial ring sources flanking the ring detector on alternating sides of the ring detector and configured to emit radiation toward the ring detector.

34. The system of claim 24, wherein the at least one stationary distributed X-ray source includes one or more partial ring sources and wherein the at least one stationary detector includes one or more notched detectors.

35. The system of claim 24, wherein the at least one stationary detector includes a helical detector, and wherein the at least one stationary distributed X-ray source includes a helical source placed adjacent to the helical detector.

36. A method of X-ray imaging comprising:
providing at least one stationary detector extending generally around at least a portion of an imaging volume;
providing at least one stationary distributed X-ray source placed adjacent to the at least one detector configured to emit radiation toward the detector;
providing a source controller for triggering one or more emitters in the at least one stationary distributed X-ray source for acquiring volumetric data by the at least one stationary detector, wherein the at least one stationary detector and the at least one stationary distributed X-ray source are configured to cooperate to contribute towards mathematical completeness of acquired volumetric data for image reconstruction; and
measuring additional data by employing line sources.

37. A method of X-ray imaging comprising:
providing at least one stationary detector extending generally around at least a portion of an imaging volume;
providing at least one stationary distributed X-ray source placed adjacent to the at least one detector configured to emit radiation toward the detector;
providing a source controller for triggering one or more emitters in the at least one stationary distributed X-ray source for acquiring volumetric data by the at least one stationary detector,
wherein the at least one stationary detector and the at least one stationary distributed X-ray source are configured to cooperate to contribute towards mathematical completeness of acquired volumetric data for image reconstruction; and
providing one or more ring detectors placed between two or more ring sources.

38. The method of claim 37 wherein at least one of a source and a detector is configured to make a telescopic movement for allowing adaptive Z-coverage.

39. A volumetric stationary CT system comprising:
at least two stationary detectors extending generally around at least a portion of an imaging volume;
at least one stationary distributed X-ray source placed proximal to the at least two stationary detectors;
a source controller for triggering one or more emitters in the at least one stationary distributed X-ray source for acquiring volumetric data by the at least two stationary detectors,
wherein the at least two stationary detectors and the at least one stationary distributed X-ray source are configured to cooperate to contribute towards mathematical completeness of acquired volumetric data for image reconstruction; and
one or more line sources extending at least along a Z-direction to increase mathematical completeness in acquired volumetric data for image reconstruction.

* * * * *